US011363972B2

(12) United States Patent
Ko et al.

(10) Patent No.: US 11,363,972 B2
(45) Date of Patent: *Jun. 21, 2022

(54) SENSOR CABLE SUPPORT DEVICE INCLUDING MECHANICAL CONNECTORS

(71) Applicant: DexCom Inc., San Diego, CA (US)

(72) Inventors: Pey-Jiun Ko, Redwood City, CA (US);
Arthur Lin, Fremont, CA (US);
Timothy Stowe, Alameda, CA (US)

(73) Assignee: DexCom, Inc., San Diego, CA (US)

( * ) Notice: Subject to any disclaimer, the term of this patent is extended or adjusted under 35 U.S.C. 154(b) by 20 days.

This patent is subject to a terminal disclaimer.

(21) Appl. No.: 17/112,876

(22) Filed: Dec. 4, 2020

(65) Prior Publication Data
US 2021/0085222 A1 Mar. 25, 2021

Related U.S. Application Data

(63) Continuation of application No. 16/899,503, filed on Jun. 11, 2020, now abandoned, which is a
(Continued)

(51) Int. Cl.
*G05D 11/00* (2006.01)
*A61B 5/145* (2006.01)
(Continued)

(52) U.S. Cl.
CPC .......... *A61B 5/1451* (2013.01); *A61B 5/1473* (2013.01); *A61B 5/14503* (2013.01);
(Continued)

(58) Field of Classification Search
CPC ....... H02J 3/14; H04H 20/67; G05B 19/0421; G05B 15/02; G05B 13/024; G06F 17/40;
(Continued)

(56) References Cited

U.S. PATENT DOCUMENTS

| 1,534,265 A | * | 4/1925 | Harrison | ................ A47G 25/20 223/88 |
| 5,626,479 A | * | 5/1997 | Hughes | ................ H01R 31/065 439/651 |

(Continued)

OTHER PUBLICATIONS

International Preliminary Report on Patentability for Application No. PCT/US2019/024605, dated Oct. 8, 2020, 10 pages.
(Continued)

*Primary Examiner* — Phuong Chi Thi Nguyen
(74) *Attorney, Agent, or Firm* — Snell & Wilmer LLP

(57) ABSTRACT

A sensor cable support device is described. The sensor cable support device can be used to implemented in wearable monitoring device to support a proximal portion of a sensor cable and electrically connect the proximal portion with a sensing circuitry. A distal portion of the sensor cable is insertable into a person's skin. The sensor cable support device may include a rigid body defining a pair of openings, a set legs attached to the rigid body, and a pair of electrical traces extending between the pair of openings and distal ends of a pair of legs of the set of legs. The pair of openings may be sized and configured to receive a pair of pucks that mechanically retain a sensor cable to the body and electrically connect the sensor cable with the electrical traces.

12 Claims, 6 Drawing Sheets

Related U.S. Application Data continuation of application No. 16/779,461, filed on Jan. 31, 2020, now Pat. No. 10,729,360, which is a continuation of application No. 16/368,100, filed on Mar. 28, 2019, now Pat. No. 10,588,551.

(60) Provisional application No. 62/649,350, filed on Mar. 28, 2018.

(51) Int. Cl.
| | |
|---|---|
| *A61B 5/1473* | (2006.01) |
| *A61B 5/00* | (2006.01) |
| *H05K 1/18* | (2006.01) |
| *H05K 7/14* | (2006.01) |

(52) U.S. Cl.
CPC ........ *A61B 5/14532* (2013.01); *A61B 5/6801* (2013.01); *A61B 5/6833* (2013.01); *A61B 5/6847* (2013.01); *H05K 1/181* (2013.01); *H05K 7/1427* (2013.01); *A61B 2560/0462* (2013.01); *A61B 2562/12* (2013.01); *A61B 2562/225* (2013.01); *H05K 2201/10151* (2013.01); *H05K 2201/10356* (2013.01)

(58) Field of Classification Search
CPC .......... H04L 29/08108; H04L 29/06027; H03J 9/002; H03J 9/04; H04W 8/245
See application file for complete search history.

(56) References Cited

U.S. PATENT DOCUMENTS

| | | | |
|---|---|---|---|
| 8,170,722 B1 * | 5/2012 | Elberbaum | H04L 12/281 |
| | | | 455/92 |
| 8,403,680 B2 * | 3/2013 | Schultz | H05K 1/0233 |
| | | | 439/38 |
| 9,209,558 B2 | 12/2015 | Greig et al. | |
| 9,634,435 B1 | 4/2017 | Raschilla et al. | |
| 10,029,107 B1 | 7/2018 | Webb et al. | |
| 10,446,979 B1 | 10/2019 | Liu | |
| 10,588,551 B2 | 3/2020 | Ko et al. | |
| 2006/0014421 A1 | 1/2006 | Nanda et al. | |
| 2007/0208244 A1 | 9/2007 | Brauker et al. | |
| 2016/0181744 A1 | 6/2016 | Kao et al. | |
| 2016/0254613 A1 * | 9/2016 | Choi | H01R 13/5829 |
| | | | 439/31 |
| 2017/0112534 A1 | 4/2017 | Schoonmaker et al. | |
| 2018/0054023 A1 | 2/2018 | Greig et al. | |
| 2018/0181744 A1 | 6/2018 | Baentsch et al. | |
| 2020/0170550 A1 | 6/2020 | Ko et al. | |

OTHER PUBLICATIONS

International Search Report and Written Opinion for Application No. PCT/US2019/024605 dated Aug. 21, 2019, 13 pages.
Office Action from European Patent Application No. 19720000.9, dated Nov. 4, 2020, 3 pages.

\* cited by examiner

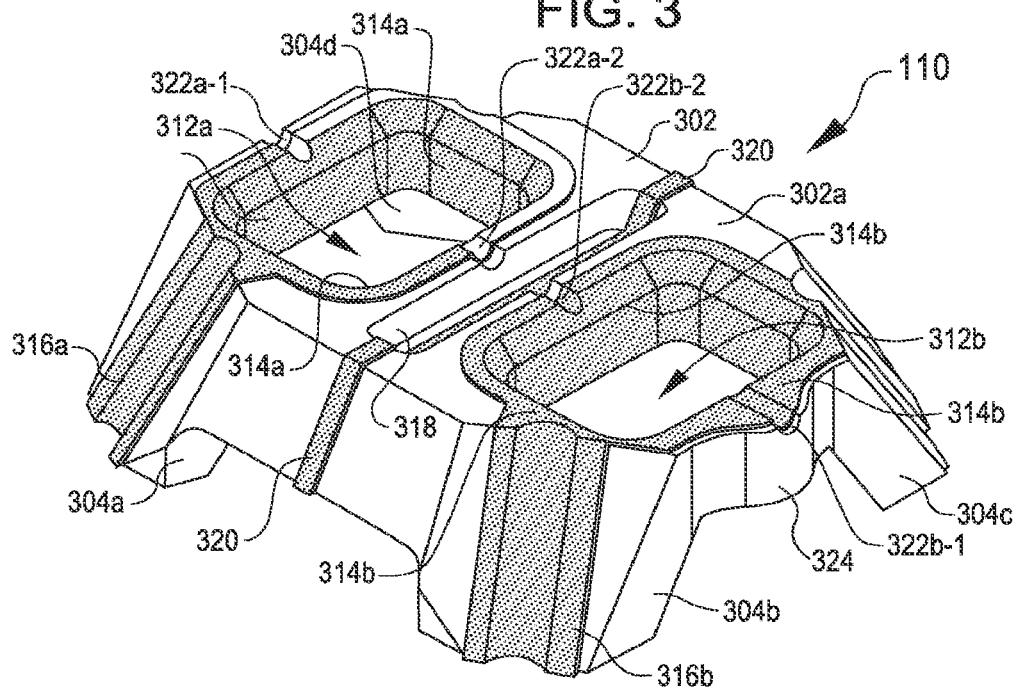
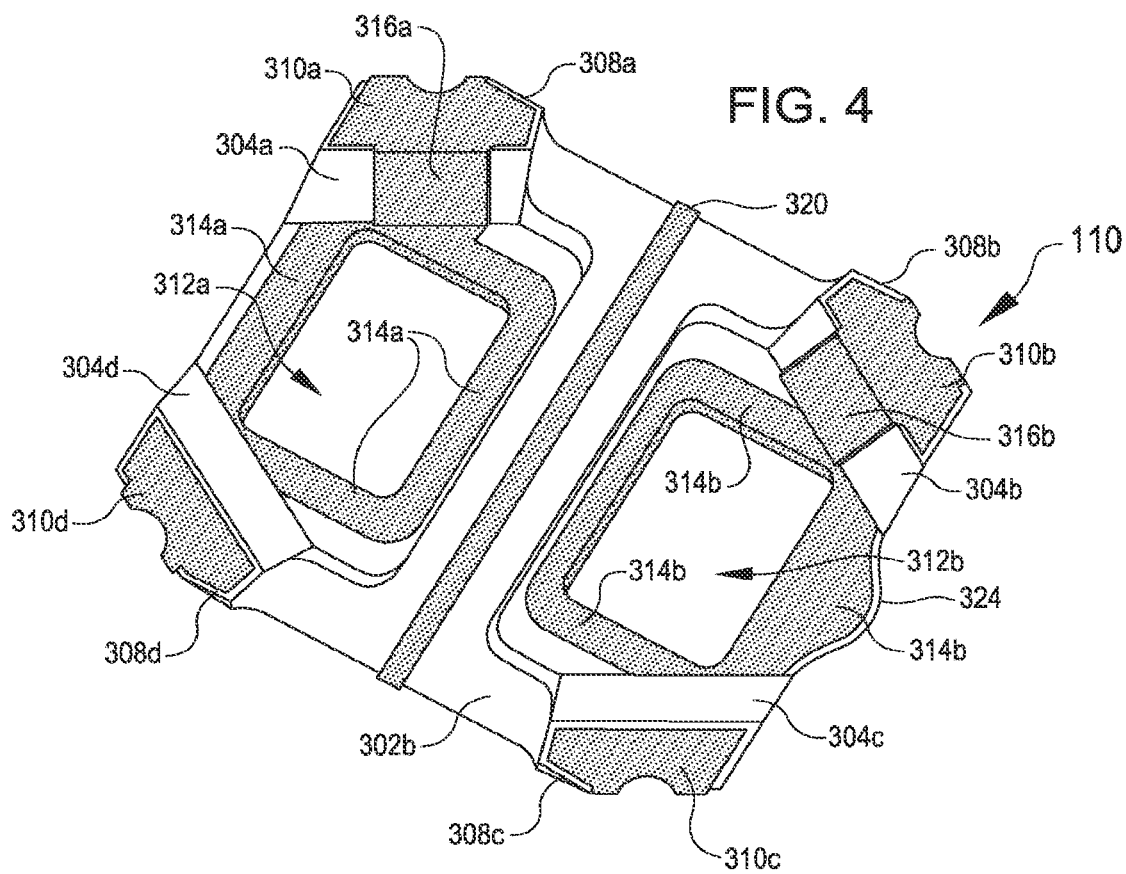

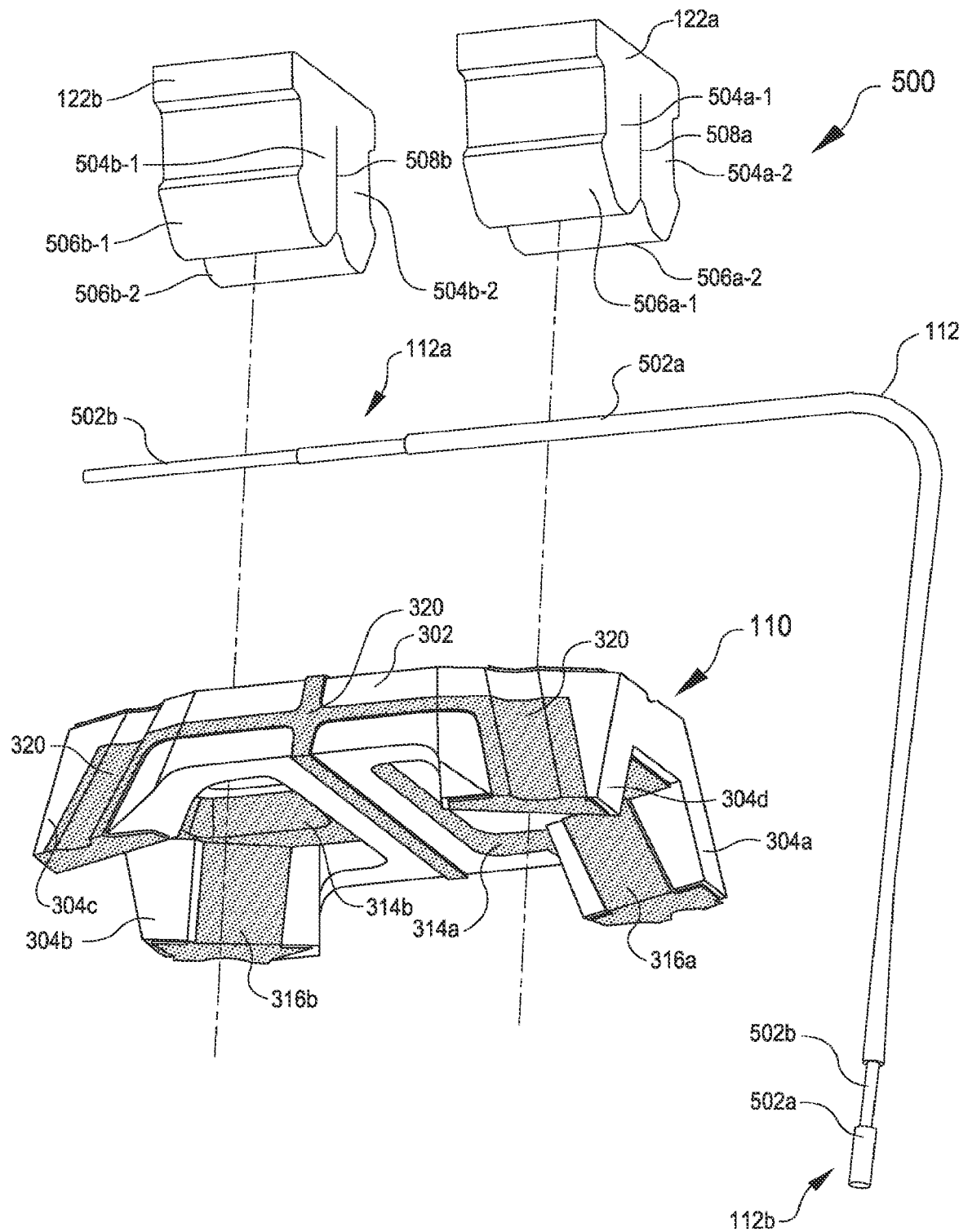

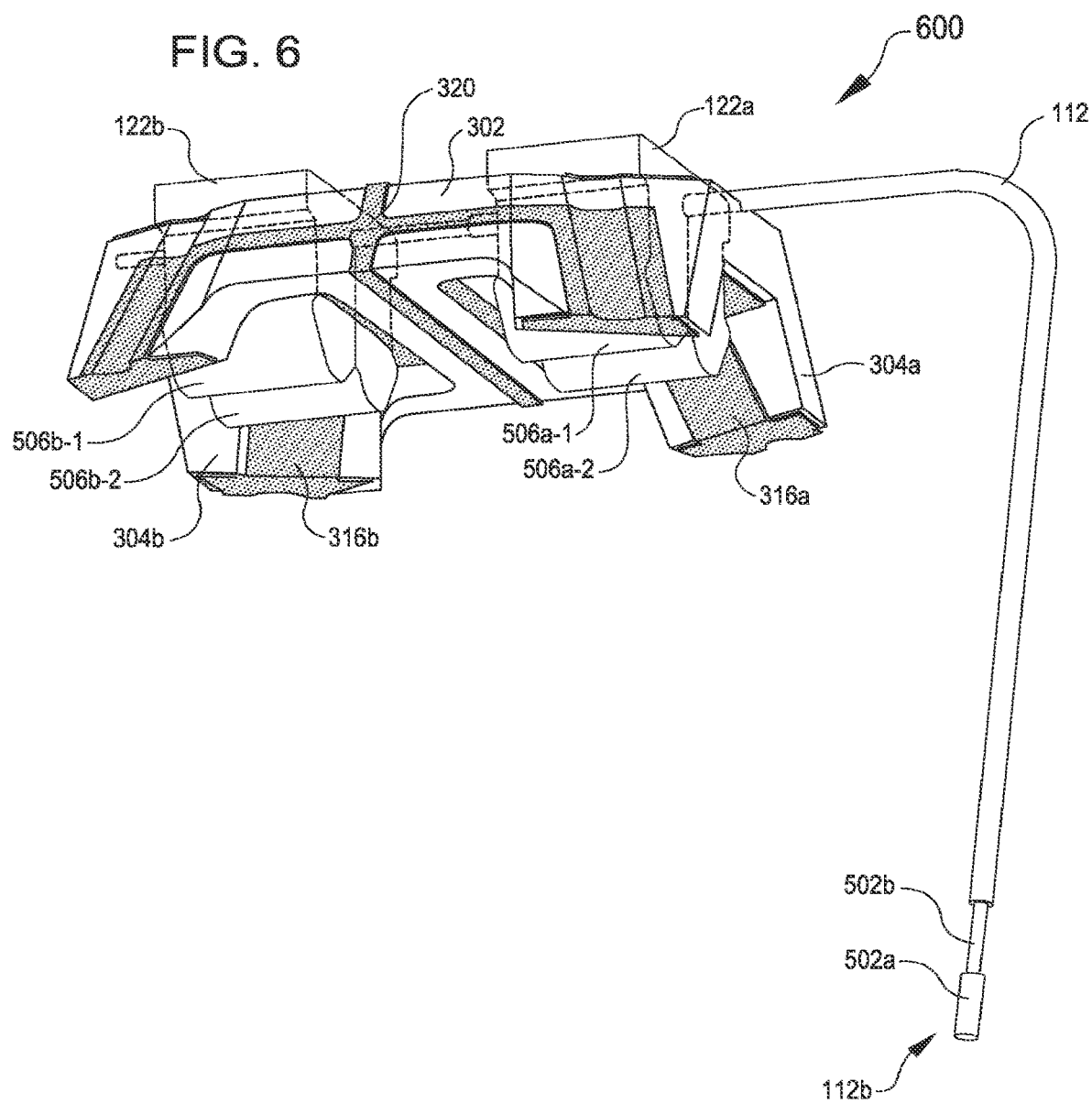

SENSOR CABLE SUPPORT DEVICE INCLUDING MECHANICAL CONNECTORS

CROSS-REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 16/899,503, filed Jun. 11, 2020, which is a continuation of U.S. application Ser. No. 16/779,461, filed Jan. 31, 2020, now U.S. Pat. No. 10,729,360, which is a continuation of U.S. application Ser. No. 16/368,100, filed Mar. 28, 2019, now U.S. Pat. No. 10,588,551, which claims priority to U.S. Provisional Patent Application No. 62/649,350, filed Mar. 28, 2018. Each of the aforementioned applications is incorporated by reference herein in its entirety, and each is hereby expressly made a part of this specification.

BACKGROUND

Invasive biosensors, such as sensors for wearable monitoring devices, include thin sensor wires or electrodes that are insertable into a patient's skin. Sensing circuitry reads biological information about the patient via the thin wires. To use some devices, patients or medical professionals are required to connect the sensor wires to the sensing circuitry. For example, the sensor wires may be implanted into the patient's skin during a first step, and, during a second step, the sensor wires may be connected to a monitoring device. This two-step approach may be overly complicated for some patients to perform on their own and/or may be cost prohibitive to have a medical professional perform. In addition, such devices may include multiple openings by which wires and the sensing circuitry may be exposed to potential moisture that may significantly impact performance of the biosensor.

Preassembling the sensor wires within the monitoring device is a possibility. For example, proximate portions of the sensor wires can be soldered or welded to a printed circuit board within the monitoring device. Exposure of the sensor wires to such high localized temperatures associated with soldering and welding, however, may damage the sensor wires; especially, if the sensor wires have been coated with a membrane. Additionally, such approaches may result in sensor wires that are unsuitably rigid as a result of the soldering and/or welding.

In addition to the considerations above, the size of the monitoring device is a practical consideration for wearable devices. To accommodate the required sensing circuitry, power source, and the like to process the biological information, wearable monitoring devices may include multiple parts that are coupled together to form working devices. Not only does the use of multiple parts cause the devices to be bulky, but it also creates multiple areas for possible moisture ingress (e.g., seals between parts).

SUMMARY

One general aspect includes a support device for supporting a sensor cable, the support device, includes a rigid body defining a pair of openings. Each opening is sized and configured to receive a conductive puck. The rigid body is configured to support a proximal end of the sensor cable and electrically couple the sensor cable with sensing circuitry of a monitoring device. The support device also includes a set of rigid legs connected to the rigid body and extending away from bottom side of the rigid body. The support device also includes a first electrical trace electrically coupling a first opening of the pair of openings and a distal end of a first leg of the set of rigid legs. The support device also includes a second electrical trace electrically coupling a second opening of the pair of openings and a distal end of a second leg of the set of rigid legs.

Another general aspect includes a wearable monitoring device, including: a printed circuit board disposed in a housing having an exterior surface for positioning the wearable monitoring device on a person's skin. The wearable monitoring device also includes sensing circuitry including one or more electronic components connected to the printed circuit board. The wearable monitoring device also includes and a sensor holder system, including a body having a set of legs that extends from one side of the body. The sensor holder system is physically coupled to the printed circuit board via the set of legs. The body has a pair of conductive openings formed therein. The pair of conductive openings is electrically coupled to the printed circuit board. The sensor holder system also includes a sensor cable electrically coupled to the sensing circuitry and including a first portion in electrical contact with a first conductive opening of the pair of conductive openings to form a first electrical connection and a second portion in electrical contact with a second conductive opening of the pair of conductive openings to form a second electrical connection. The sensor holder system also includes a pair of pucks installed in the pair of conductive openings such that a first puck of the pair of pucks mechanically retains the first portion in electrical contact with the first conductive opening and a second puck of the pair of pucks mechanically retains the second portion in electrical contact with the second conductive opening.

Yet another general aspect includes an analyte monitoring system, including a sensor cable including a first portion insertable into skin of a person, the first portion including means for generating glucose information. The analyte monitoring system also includes a sensor holder system, including alignment means for physically aligning a second portion of the sensor cable. The sensor holder system also includes retaining means for physically retaining the second portion of the sensor cable. The sensor holder system also includes support means for physically supporting the alignment means and the retaining means. The sensor holder system also includes coupling means for electrically coupling the second portion of the sensor cable to circuitry disposed on a printed circuit board for determining an analyte level for the person.

Yet another general aspect includes a sensor cable support system, including a sensor cable support device. The sensor cable support device also includes a body having a pair of conductive openings. The sensor cable support device also includes a set of legs extending away from a bottom side of the body. The sensor cable support device also includes a pair of electrical traces extending between the pair of conductive openings and distal ends of a pair of legs of the set of legs. The sensor cable support system also includes a sensor cable including a first portion in electrical contact with a first conductive opening of the pair of conductive openings to form a first electrical connection. The sensor cable also includes a second portion in electrical contact with a second conductive opening of the pair of conductive openings to form a second electrical connection. The sensor cable support system also includes a pair of pucks installed in the pair of conductive openings such that a first puck of the pair of pucks mechanically retains the first portion in electrical contact with the first conductive opening and a second puck of the pair of pucks mechanically retains the second portion in electrical contact with the second conductive opening.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 3 illustrates a top, perspective view of a sensor cable support device, according to at least one example.

FIG. 4 illustrates a bottom, perspective view of the sensor cable support device of FIG. 3, according to at least one example.

FIG. 5 illustrates an exploded, perspective view of an example of a sensor holder system including a sensor cable support device, according to at least one example.

FIG. 6 illustrates a bottom, perspective view of the sensor holder system of FIG. 5, according to at least one example.

DETAILED DESCRIPTION

Figure 1:
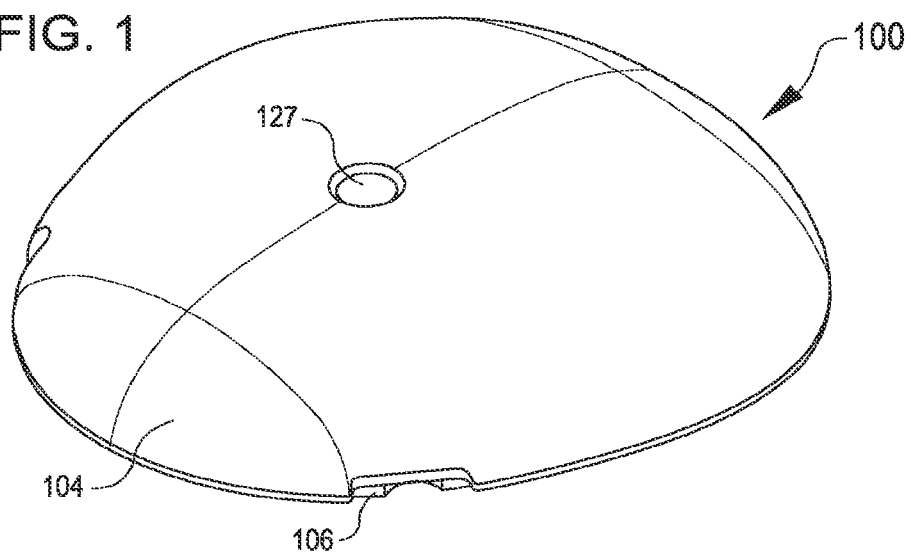
FIG. 1 illustrates a perspective view of a monitoring device that may include a sensor cable support device, according to at least one example.

Examples are described herein in the context of sensor cable support devices for use in continuous monitoring devices. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a wearable glucose monitoring device (e.g., a body-mountable device such as a subcutaneous monitoring device) or system includes a glucose sensor that can be inserted into a person's skin for continuous monitoring of the person's glucose levels. While being worn, the wearable glucose monitoring device may be exposed to normal external forces resulting from clothing, bumping up against obstacles, and other external forces. To reduce the impact of these forces and to improve wearer comfort, the footprint and the profile of the glucose monitoring device may be reduced. As a way to do so, the glucose monitoring device described herein includes a sensor cable support device. The sensor cable support device has a unique shape that enables it to perform various functions, while also efficiently utilizing space in the glucose monitoring device. The unique shape is defined by a body that is supported by legs that extend from the body. The legs are connected to a primed circuit board ("PCB") below the body and function to space the body apart from the PCB. The height of the sensor cable support device holds the sensor cable off from the PCB. This allows for use of a longer sensor cable resulting in a more gentle radius of curvature as the sensor cable exits the wearable glucose monitoring device towards the person's skin. Components of the glucose monitoring device such as an integrated circuit and/or other sensing circuitry may be installed below the body, within a void formed under the body. In this manner, the sensor cable support device provides for efficient use of space in the glucose monitoring device (e.g., allows for stacking of components and reduces an overall footprint of the device).

The functions performed by the sensor cable support device include structurally supporting electrodes proximal of the glucose sensor included in the sensor cables, aligning sensor cables of the glucose sensor toward the person's skin, and electrically connecting the electrodes to the PCB. The sensor cable support device structurally supports the electrodes by way of a pair of electrically conductive elastomeric pucks or other similar mechanical connectors that are inserted into corresponding conductive holes in the body of the sensor cable support device. The conductive puck and hole approach for connecting the electrodes avoids potential damage to the electrodes from exposure to high heat. And unlike methods that rigidly attach the electrodes to the sensor cable support device, the puck and hole approach provides passive strain relief based on the elastomeric properties and geometry of the pucks as compared to the electrodes and the holes. The puck and hole approach also electrically connects the electrodes to conductive surfaces adjacent to and/or within the conductive holes. Each hole is electrically connected to the PCB by way of an electrical trace that extends from the hole, down a leg, and terminates at a distal end of the leg that is connected to the PCB. The sensor cable support device also aligns the sensor cables by way of a set of grooves that extend across the holes. For example, a first groove extending across a first hole is aligned with a second groove extending across a second hole. In this manner, a first and second coaxial electrode of a sensor cable can be held respectively in the first grove and the second groove. While the sensor cable support device is described herein with reference to a wearable glucose monitoring device, it is understood that the sensor cable support device may be implemented to support any suitable body-mountable electromechanical sensor (e.g., subcutaneous monitoring systems, deep brain stimulators, cochlear implants, cardiac pacemakers, bioelectric devices, and other similar devices).

In an example, a sensor cable support device is described. The sensor cable support device includes: a rigid body having a pair of openings, each opening is sized and configured to receive a conductive puck. The sensor cable support device also includes a set of legs attached to the rigid body and extending from one side of the rigid body. The set of legs may include one or more members that extend distally from a bottom portion of the rigid body. For example, proximal portions of the members can be connected to the rigid body on an underside of the rigid body. These members can extend away from the underside in substantially the same direction. When the sensor cable support device is mounted to a mounting surface (e.g., a printed circuit board of a monitoring device), the set of legs support the rigid body in an orientation that is spaced apart from the mounting surface. The set of legs can include members that are integral to the rigid body, members that external to the rigid body but connected or otherwise bonded to the rigid body, and other similar members that extend below the body and between the rigid body and the mounting surface. The sensor cable support device also includes a first electrical trace electrically coupling a first opening of the pair of openings and a distal end of a first leg of the set of legs. For example, the first opening can include a conductive ring within the opening and the first electrical trace can extend between the conductive ring and distal end of the first leg. In some examples, the first electrical trace is formed in the first leg using a laser direct structuring technique. In this manner, the first electrical trace may be visible at an exterior surface of the first leg. The sensor cable support device also includes a second electrical trace electrically coupling a second opening of the pair of openings and a distal end of a second leg of the set of legs. The second electrical trace may resemble the first electrical trace is design and function.

In another example, a wearable monitoring device is described. A wearable device may include any kind of device that may be worn by an individual; may be physically attached to the user, such as by an adhesive or mounting device such as a clip; may be partially or entirely embedded in a person, such as by insertion of a portion of the device into the wearer's skin (e.g., a sensor wire) or implanted entirely beneath their skin; etc. The wearable monitoring device includes: a printed circuit board disposed in a housing having an exterior surface for positioning the wearable monitoring device on skin of a person. The wearable monitoring device also includes sensing circuitry including one or more electronic components connected to the printed circuit board; and a sensor cable support system. The sensor cable support system includes a body having a set of legs that extends away from a bottom side of the body. For example, the set of legs can be connected proximally at a bottom side surface of the body, with ends extending distally away from the bottom side surface. The set of legs can also be connected proximally at a perimeter of edge of the bottom side surface, at a perimeter edge of a top side surface, at a set of side walls of the body, and at any other suitable location on the body. In some examples, the body has a roughly rectangular shape and each leg of the set of legs is extends away from a bottom side a corner of the body. The sensor cable support device can be physically coupled to the primed circuit board via the set of legs. The body can have a pair of conductive openings formed therein. For example, the conductive openings can be holes that extend through the body (e.g., from a top side to a bottom side) and include conductive plating disposed within and around the perimeters of the holes. In some examples, a conductive ring is fitted within each opening. The pair of conductive openings can be electrically isolated from each other. Each conductive openings can be electrically coupled to the printed circuit board via an electrical trace that extends between the conductive opening and a distal end of one of the legs. The sensor cable support system also includes a sensor cable including two wires that are electrically coupled to the sensing circuitry via first and second electrically isolated electrical connections. The sensor cable includes a first portion of a first wire in electrical contact with a first conductive opening of the pair of conductive openings to form the first electrical connection and a second portion of a second wire in electrical contact with a second conductive opening of the pair of conductive openings to form the second electrical connection. The sensor holder system also includes a pair of conductive elastomeric pucks installed in the pair of conductive openings such that a first puck of the pair of pucks mechanically retains the first portion of the first wire in electrical contact with the first conductive opening and a second puck of the pair of pucks mechanically retains the second portion of the second wire in electrical contact with the second opening.

In another example, a glucose monitoring device is described. The glucose monitoring device includes: a sensor cable including a first distal portion insertable into skin of a person, the first distal portion including means for generating glucose information (e.g., distal portions of two or more wires including distal terminals); and a sensor cable support system. The sensor cable support system also includes alignment means for physically aligning a second portion of the sensor cable (e.g., proximal portions of the two or more wires). The sensor cable support system also includes retaining means for physically retaining the second portion of the sensor cable. The sensor cable support system also includes support means for physically supporting the alignment means and the retaining means. The glucose monitoring system also includes coupling means for electrically coupling the second portion of the sensor cable to circuitry disposed on a printed circuit board for determining a glucose level for the person.

In another example, a sensor cable support system is described. The sensor cable support system includes: a sensor cable support device, including: a body having a pair of conductive openings formed therein. The sensor cable support device also includes a set of legs extending away from a bottom side of the body. The sensor cable support device also includes a pair of electrical traces extending between the pair of conductive openings and distal ends of a pair of legs of the set of legs. The sensor holder system also includes a sensor cable including a first portion in electrical contact with a first conductive opening of the pair of conductive openings to form a first electrical connection; and a second portion in electrical contact with a second conductive opening of the pair of conductive openings to form a second electrical connection. The sensor cable support system also includes a pair of pucks installed in the pair of openings such that a first puck of the pair of pucks mechanically retains the first portion of the sensor cable in physical contact with the first conductive opening and a second puck of the pair of pucks mechanically retains the second portion of the sensor cable in physical contact with the second opening.

Figure 2:
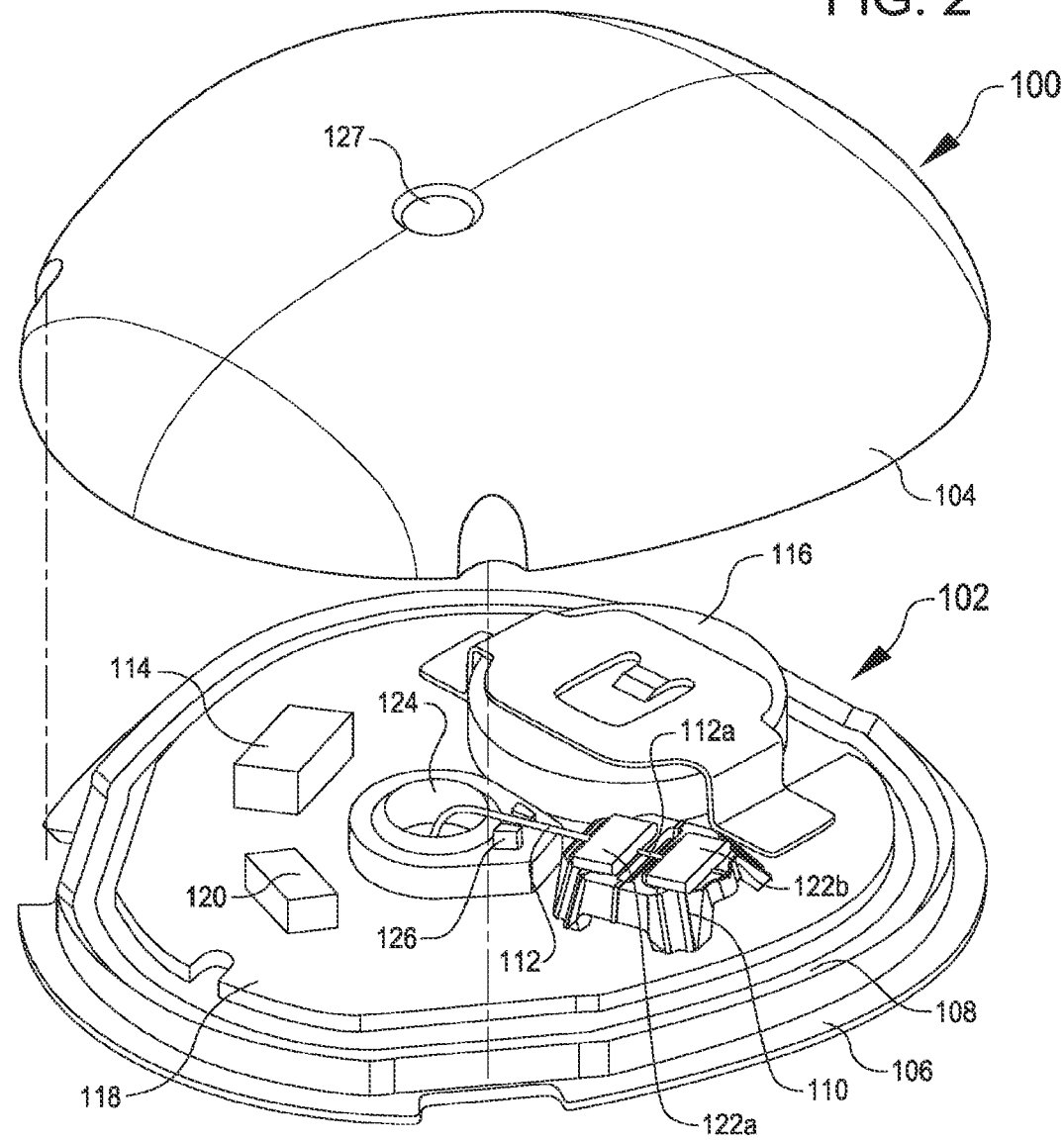
FIG. 2 illustrates a partially exploded view of the monitoring device of FIG. 1 with a top enclosure removed, according to at least one example.

Turning now to the Figures, FIGS. 1 and 2 respectively illustrate a perspective view of a monitoring device 100 and a partially, exploded view of the monitoring device 100 including a biosensor 102, according to various examples. The monitoring device 100 may be a wearable monitoring device that is mounted to a body at an exterior surface (e.g., against a person's skin), held against the body at the exterior surface, implanted within the body (e.g., subcutaneously beneath the person's skin), or mounted in any other suitable manner. The monitoring device 100 includes a top enclosure 104, bottom enclosure 106, a moisture barrier seal area 108, and the biosensor 102.

The top enclosure 104 and the bottom enclosure 106 together form a housing that encloses the biosensor 102 therein. As described herein, a lower portion of the housing (e.g., the bottom enclosure 106) has a substantially planar exterior surface adapted for positioning on a person's skin. An upper portion of the housing (e.g., the top enclosure 104) includes a smooth exterior surface that faces outward from the person's skin. A smooth surface, free from sharp edges, may be desirable to decrease the potential for knocking the monitoring device 100 from the person's skin once mounted. For example, the monitoring device 100 may be worn under clothing (e.g., on the person's arm), and the smooth surface decreases the potential of the person's clothing snagging on the monitoring device 100.

The biosensor 102, e.g., an analyte sensor, glucose sensor, or other electromechanical sensor for use in sensing biological information of a person, includes a sensor cable support device 110, a sensor cable 112, sensing circuitry 114, a power source 116 such as a battery, a printed circuit board ("PCB") 118, and an antenna 120. The sensor cable 112 includes a proximal end portion 112a and a distal end portion 112b (see FIG. 6). The proximal end portion 112a is supported by the sensor cable support device 110. For example, the proximal end portion 112a may be disposed within a groove or channel of the sensor cable support device 110 and physically retained by pucks 122a, 122b. The proximal end portion 112a is also electrically connected to the PCB 118 via the sensor cable support device 110. For example, as described in detail herein, the sensor cable support device 110 may include a set of electrical traces that extend proximate to a middle area of the sensor cable support device 110 toward the PCB 118. The cable alignment structure may 126 may also be integrated into the sensor cable support device 110. For example, an elongated cylindrical leg may be formed in the sensor cable support device 110 through which the sensor cable 112 may extend as it through the PCB 118. When in use, the distal end portion 112b, which includes one or more electrodes, is injected into a person's skin to measure biological parameters (e.g., glucose levels) in the interstitial fluid of subcutaneous tissue beneath the skin.

The sensor cable 112 may include a curved portion that extends through a bottom opening 124 in the PCB 118 and the bottom enclosure 106. As illustrated, a cable alignment structure 126 is included on the PCB 118 at a position adjacent to the bottom opening 124. The cable alignment structure 126 may include a pair of tabs, a groove, or other structure capable of aligning the sensor cable 112 through the bottom opening 124. The cable alignment structure 126 can be a component that is attached to the PCB 118 or may be integrated into the construction of the bottom enclosure 106 (e.g., formed at the same time and using the same approach as was used to form the bottom enclosure 106). The top enclosure 104 includes a top opening 127 that is disposed above the bottom opening 124. Through the top opening 127 may be inserted an insertion needle to inject the distal portion 112b of the sensor cable 112 underneath the person's skin. In some examples, the top opening 127 is formed from a deformable material that can reseal after the insertion needle has been inserted therethrough. In this manner, the sensor cable 112 can be injected without interrupting the moisture seal of the top enclosure 104.

In some examples, the placing the insertion needle in the bottom opening 124, with the monitoring device 100 pressed against the person's skin, may achieve the proper alignment for the insertion needle to insert the sensor cable 112 into the person's skin. In some examples, the bottom opening 124 includes a sensor guiding structure that may be used to guide the insertion needle through the monitoring device 100.

The sensor cable support device 110 may be suitably rigid to support the sensor cable 112 and, in some example, provide structural support to the PCB 118. For example, the sensor cable support device 110 may be formed from liquid crystal polymer. In some examples, the PCB 118 may be a flexible printed circuit board ("FPCB"). In this example, attaching the sensor cable support device 110 to the PCB 118 may add rigidity to the entire monitoring device 100, in addition to the flexible PCB 118.

The sensor cable support device 110 may be considered an interconnect device. For example, because the sensor cable support device 110 stands off from the PCB 118 and may stand above components (e.g., the sensing circuitry 114, the power source 116, etc.) disposed below it, the sensor cable support device 110 functions to save space within the monitoring device 100. This may result in the monitoring device 100 having a smaller footprint. In addition, because of the configuration of the sensor cable support device 110 with respect to the PCB 118, the PCB 118 may be placed close to the person's skin unlike other monitoring devices that include a standoff fixture. This provides for improved wearer comfort and less overall device bulk.

In some examples, the sensing circuitry 114 includes one or more electronic components configured for signal processing. For example, the sensing circuitry 114 may include a system on chip ("SOC") or system in package ("SIP") that includes any suitable combination components for digital signal processing, analog signal processing, mixed-signal processing, and/or the like that may be present on the surface of a PCB assembly or embedded. Such components may include, for example, a microcontroller, a memory, a timing source, one or more digital interfaces, one or more analog interfaces, clocks, voltage regulators, and/or any other suitable component. The sensing circuitry 114 may be configured to receive electrical signals from the sensor cable 112 (e.g., via the PCB 118 and the sensor cable support device 110) and process the electrical signals to determine glucose levels of the person.

In some examples, the sensing circuitry 114 includes a processing device and a computer-readable medium, such as a random access memory ("RAM") coupled to the processing device. The processing device may execute computer-executable program instructions stored in memory, such as executing one or more computer programs. Such processing devices may comprise a microprocessor, a digital signal processor ("DSP"), an application-specific integrated circuit ("ASIC"), field programmable gate arrays ("FPGAs"), state machines, or other processing means for processing electrical signals received from electrodes the sensor cable 112 (e.g., see FIG. 5). Such processing means may further include programmable electronic devices such as PLCs, programmable interrupt controllers ("PICs"), programmable logic devices ("PLDs"), programmable read-only memories ("PROMs"), electronically programmable read-only memories ("EPROMs" or "EEPROMs"), or other similar devices.

The processing device may include, or may be in communication with, media, for example computer-readable storage media, that may store instructions that, when executed by the processing device, cause the processing device to perform the steps described herein as carried out, or assisted, by a processing device. Examples of computer-readable media may include, but are not limited to a memory chip, ROM, RAM, ASIC, or any other storage means from which a processing device can read or write information.

The antenna 120 may enable transmission of information from the monitoring device 100 (e.g., to one or more electronic devices). For example, a transceiver, included in the sensing circuitry 114 or otherwise, may use the antenna 120 to transmit real-time glucose readings monitored by the biosensor 102. The transceiver may also use the antenna 120 to receive information from one or more other electronic devices (e.g., instructions to adjust settings of the biosensor 102, updates to software or firmware of the biosensor 102, etc.).

The top enclosure 104 and the bottom enclosure 106 may together form a housing for retaining the biosensor 102, with the moisture barrier 108 being disposed between the top enclosure 104 and the bottom enclosure 106. The housing may be compact in size for placing on a person's skin. The housing may be made of any suitable material for housing the biosensor 102. Non-limiting examples of materials that may be suitable for the housing include silicone, polyethylene, polyvinyl chloride ("PVC"), polypropylene, nylon, polyurethane, polycarbonate, steel, aluminum, and other plastics and metals.

The bottom enclosure 106 may include a substantially planar surface to allow the monitoring device 100 to be placed against the person's skin. The monitoring device 100 may be secured to the skin using an adhesive, band, strap, or other securing means. In some examples, the monitoring device 100 may be worn for extended period of time (e.g., days, weeks, months, etc.). When assembled, the moisture barrier 108 may create a seal that keeps moisture from infiltrating the biosensor 102. Additionally another seal may exist in between the bottom housing opening 124 and upper housing opening 127 which keeps moisture from infiltrating the biosensor. The seal may consist of an adhesive, elastomeric gasket, or other. When assembled, the top enclosure 104 encloses the biosensor 102 and mates with the bottom enclosure 106 (e.g., by way of a snap-fit, welded joint, or other). The top enclosure 104 may also be glued or otherwise bonded to the bottom enclosure 106.

FIGS. 3 and 4 respectively illustrate a top, perspective view of the sensor cable support device 110 and a bottom, perspective view of the sensor cable support device 110, according to various examples. The sensor cable support device 110, which is a type of molded interconnect device, may include a body 302 and a set of legs 304. Generally, the body 302 includes a top side or top surface 302a and a bottom side or bottom surface 302b. When installed, the top side 302a faces the top enclosure 104 and the bottom side 302b faces the PCB 118.

The top side 302a may include a substantially planar area (e.g., greater than 1 mm^2). This topside area may be suitable sized and suitably flat to allow a suction head of a robotic placement device (e.g., a pick and place device) to grasp the sensor cable support device 110.

In some examples, the sensor cable support device 110 may have a height of about 2 mm, a width of about 4 mm, and a length of about 4 mm. In other examples, the height, width, and/or length of the sensor cable support device 110 may be respectively greater than or less than 2 mm, 4 mm, and/or 4 mm. The height of about 2 mm may be selected to be less than the height of the power source 116. The height of about 2 mm may also provide a suitable separation between the proximal end portion 112a of the sensor cable 112 and the sensing circuitry 114 and other electronic components attached to or otherwise disposed on or within the PCB 118.

The set of legs 304 extend from one side of the body 302, extend below the body 302, and, in some examples, include a corresponding set of feet 308. For example, the body 302 may be oriented in a first plane and the set of feet 308 may be oriented in a second, different plane. The set of legs 304 may extend between the first plane and the second plane to connect the body 302 to the set of feet 308. The body 302 may be oriented in the first plane when a substantial portion of the body 302 is located in the first plane. The set of feet 308 (e.g., distal ends of the set of legs 304) may be oriented in the second plan when substantial portions of the set of feet 308 is located in the second plane. In some examples, the set of feet 308 may include conductive pads 310. The sensor cable support device 110 may be electrically and structurally attached to the PCB 118 or other structure using the conductive pads 310. In some examples, the feet 308 are connected to the PCB 118 using surface mount technology.

Within the body 302 may be formed a pair of conductive openings 312. The conductive openings 312 may extend through the body 302 from the top side 302a to the bottom side 302b. In some examples, the conductive openings 312 are defined as cavities which do not extend through the body 302. In any event, the conductive openings 312 may be sized and configured to receive the pucks 122. With respect to sizing, the conductive openings 312 may have a rectangular cross section, but it is understood that any other cross sectional shape may be used (e.g., square, circular, oval, etc.). With respect to configuration, the conductive openings 312 may include geometric features that correspond to those of the pucks 122 such that the pucks 122, when installed, retain the sensor cable 112 in contact with the body 302.

The conductive surfaces 314a, 314b, shown in the FIGS. by hatching, are disposed within the conductive openings 312. The conductive surface 314a, which may include a conductive material that has been applied or otherwise deposited on the inward and outward facing surfaces of the conductive opening 312a, may be electrically coupled to an electrical trace 316a. The electrical trace 316a extends from the conductive surface 314a, along the leg 304a, and connects with the conductive pad 310a. Similarly, the conductive surface 314b, which may include a conductive material that has been applied or otherwise deposited on the inward and outward facing surfaces of the conductive opening 312b, may be electrically coupled to an electrical trace 316b. The electrical trace 316b extends from the conductive surface 314b, along the leg 304b, and connects with the conductive pad 310b. In this manner, the conductive surface 314a and the electrical trace 316a are electrically isolated from the conductive surface 314b and the electrical trace 316b. The electrical traces 316 may extend along an outside surface of the sensor cable support device 110 and/or may be disposed within the sensor cable support device 110.

To further electrically isolate the conductive surface 314a from the conductive surface 314b, an electrical guard structure 318 may be formed within the body 302. The purpose of the electrical guard structure 318 is to minimize current leakage between the conductive openings 312a, 312b. The electrical guard structure 318 can be any suitable cavity, channel, hole, opening, or structure that is disposed between two electrically isolated contacts. In some examples, electrical guard structure 318 functions like a guard trace to minimize crosstalk between two traces.

In some examples, the electrical guard structure 318 includes a channel or hole in the top side 302a, an opening that extends from the top side 302a to the bottom side 302b, and/or a guard trace 320. The guard trace 320, as illustrated in FIGS. 3-6, may extend from the top side 302a to the bottom side 302b, along a back side (as shown in FIGS. 5 and 6), and along one or more legs 304 (e.g., 304c, 304d). Like the electrical traces 316, the guard trace 320 may terminate at one or more conductive pads 310 (e.g., 310c, 310d), by which the guard trace 320 may be electrically coupled to the PCB 118.

A groove 322 can be formed in the top side 302a of the body 302 of the sensor cable support device 110. The groove 322 can span the two conductive openings 312. In some examples, the groove 322 is defined to include groove parts 322a-1, 322a-2, 322b-1, and 322b-2. The groove parts 322a correspond to the conductive opening 312a and extend through at least a portion of the conductive surface 314a and a portion of the top side 302a adjacent to the conductive opening 312a. Likewise the groove parts 322b correspond to the conductive opening 312b and extend through at least a portion of the conductive surface 314b and a portion of the top side 302a adjacent to the conductive opening 312b. The groove 322 is sized to correspond to the sensor cable 112. In particular, the groove parts 322a are sized to correspond to a first portion of the sensor cable 112 (e.g., a first electrode having a first cross sectional area) and the groove parts 322b are sized to correspond to a second portion of the sensor cable 112 (e.g., a second electrode having a second cross sectional area). In some examples, the groove 322 has a consistent shape and size. The groove parts 322a and 322b can be aligned in a coaxial manner such that an elongate straight sensor cable 112 can contact all groove parts 322a and 322b.

Use of the groove 322 may enable one or more independent electrical contact points between the sensor cable 112 and the conductive surface 314 (e.g., at the groove parts 322a-1, 322a-2, 322b-1, and 322b-2). Additionally, when the pucks 122 are also conductive, the number of contacts points increases even more. For example, the pucks 122 may physically contact one or more interior faces of the conductive openings 312 where the conductive surface 314 is disposed, forming more surfaces for electrical contact.

The sensor cable support device 110 may also include an orientation structure 324. The orientation structure 324 may be used to orient and/or align the sensor cable support device 110 during assembly and/or to align the top enclosure 104 with the bottom enclosure 106.

The sensor cable support device 110 may be formed in any suitable manner including, for example, injection molding, or other suitable techniques. The sensor cable support device 110 may be formed as a single piece including at least the body 302, the legs 304, and/or the feet 308. The sensor cable support device 110 may be formed from any suitable material including, for example, liquid crystal polymer (e.g., RTP 3499-3 X 113393 A sold by RTP Co., VECTRA® E840i LDS sold by Ticon, etc.), high-temperature nylon, polyetheretherketone ("PEEK"), and other similar materials. In some examples, the material selected for the sensor cable support device 110 may be non-conductive, have low moisture absorption properties, have low water vapor transmission rates, and may be easily moldable into very thin walls. In some examples, the material selected for the sensor cable support device 110 may be capable of LDS processing. The rigidity of the sensor cable support device 110 may depend on one or both of the sensor cable support device's 110 thickness and the material forming the sensor cable support device 110. For example, the sensor cable support device's 110 thickness may be inversely proportional to the density of the material (e.g., a denser material may allow for a thinner sensor cable support device 110 while a less dense material may require a thicker sensor cable support device 110).

The electrical traces 316, 320 and the conductive surfaces 314 (and any other conductive pathways or surface) may be formed in the sensor cable support device 110 using any suitable technique. Examples of such techniques include LDS processing and corresponding techniques for depositing a conductive material such as copper, nickel, gold, etc. in a circuit pattern. Such techniques may include electroless copper plating. For example, such techniques may include those using Enplate® LDS AG-600 as sold by Enthone®. The electrical traces 316, 320 and the conductive surfaces 314 may have a thickness of about 1 micron. In some examples, the electrical traces 316, 320 and the conductive surfaces 314 have a thickness of less than 1 micron (e.g., 0.25 microns to 0.5 microns). In some examples, the electrical traces 316, 320 and the conductive surfaces 314 may be formed using other plating techniques.

FIGS. 5 and 6 respectively illustrate a top, exploded perspective view of a sensor holder system 500 and a bottom, perspective view of the sensor holder system 500, according to various examples. The sensor holder system 500, in this example, is defined to include the sensor cable support device 110, the sensor cable 112, and the pucks 122.

The sensor cable 112 may include one or more electrodes, chemicals, or other means for generating biological information. For example, the sensor cable 112 may be a coaxial sensor and include two electrodes 502a, 502b that are inserted into the person's skin to expose the electrodes 502a, 502b to the interstitial fluid in the person's subcutaneous tissue. In some examples, the sensor cable 112 may include two or more separate wires that are not included in the same coating. The electrode 502b includes at least a portion of the sensor cable 112 made of platinum or having a platinum coating and electrode 502a includes a silver/silver-chloride ("Ag/AgCl") material that covers a part of electrode 502b. The electrodes 502b, 502a may be used to generate glucose information about the person by generating electrical signals corresponding to an amount of glucose present within the interstitial fluid. In some examples, a reactive material, such as glucose oxidase ("GOX"), may also be coated on a distal end of the electrode 502b to create reaction products with glucose present in the interstitial fluid. When a voltage is applied to the electrodes 502b, 502a, an electrical current is generated based on the amount of these reaction products generated by the glucose/GOX reaction. The electrical current is routed through the sensor cable 112 to the sensing circuitry 114. The sensing circuitry 114 may use the strength of the current to determine glucose information such as the person's glucose levels. Although glucose level measurements are described in this example, the biosensor 102 may be configured to measure other biological parameters without departing from the scope of the present disclosure. Similarly, while the chemical materials applied onto the sensor cable 112 to form the electrodes 502b, 502a and the reactive material coated onto the electrodes 502b, 502a may be suitable for a glucose sensor, other material may be used according to other examples, based on the application of the biosensor 102.

The sensor cable's 112 length may allow the sensor cable 112 to extend from beneath the person's skin to the sensor cable support device 110 with allowance for the person's movement. For example, the sensor cable 112 may be between approximately 10 millimeters to 30 millimeters long. The sensor cable's 112 thickness, or gauge, may be selected to allow the sensor cable 112 to remain injected into the skin during this period with minimal discomfort. In some examples, the sensor cable 112 includes an outer diameter of approximately 100-200 microns for portions of the cable coated with the electrode 502a and an outer diameter of approximately 100 microns for the electrode 502b. In additional examples, the sensor cable 112 generally may have a maximum outer diameter approximately between 100 microns and 300 microns. In some examples, however, the sensor cable 112 may have an outer diameter of about 50 microns.

Referring back to FIG. 3, in some examples, a first dimensional measurement (e.g., a width, a depth, a cross-sectional area, etc.) taken laterally across the groove 322 taken at the groove parts 322a may be different from a second dimensional measurement taken laterally across the groove 322 taken at the groove parts 322b. These differences may be included in the groove 322 to accommodate the electrodes 502a, 502b. As described herein, the electrodes 502a, 502b may be of different sizes (e.g., have different diameters). The different lateral measurements may be selected based on the respective widths of the proximate end 112a of the sensor cable at different locations. For example, one portion of the proximate end of the sensor cable 112 may be an exposed platinum electrode 502b, which may have a narrower gauge than another portion which includes the platinum wire coated with a silver/silver-chloride electrode 502a.

FIG. 5 illustrates the sensor holder system 500 in a disassembled state, e.g., the pucks 122 and the sensor cable 112 are illustrated as being removed from the conductive openings 312. FIG. 6 illustrates the sensor holder system 500 in a coupled state, e.g., the sensor cable 112 is illustrated as being held within the groove 322 and the pucks 122 are illustrated as being installed in the conductive openings 312.

The pucks 122, when installed, retain the sensor cable 112 in physical contact with the sensor cable support device 110 and electrically couple the electrodes 502 of the sensor cable 112 with the conductive surface(s) 314 in the conductive openings 312. As described herein, the pucks 122 may be formed from an electrically conductive elastomer material (e.g., silicon elastomer with carbon added or other similar material). The pucks 122 may be molded, extruded, stamped, or otherwise formed using any suitable technique.

Each puck 122 may include a pair of legs 504-1, 504-2 separated by a slit 508. The slit 508 may be sized sufficiently large to receive the proximate end portion 112a of the sensor cable 112. In some examples, the slit 508 is less than 1 mm in width. The slit 508 may also be larger or smaller than 1 mm. The slit 508 may also include a portion that corresponds in shape to an outer diameter of the sensor cable 112. For example, the slit 508 may include a cylindrical cutout at the top of the slit 508 corresponding to the sensor cable 112. In some examples, the slits 508 may be sized to accommodate the different diameters of the sensor cable 112.

The pucks 122 may be sized and configured to be installed within the conductive openings 312, in some examples, the pucks 122 are formed from a deformable conductive material that can be pressed or otherwise forced into the conductive openings 312. Once within the conductive openings, the deformable material of the pucks 122 (e.g., the pair of legs 504) expands and uses friction to hold the pucks 122 in place. In some examples, whether using deformable material or not, the legs 504 may include retaining structures 506-1, 506-2. As illustrated in FIG. 6, the retaining structures 506 may spring outwards once the pucks 122 have been installed into the conductive openings 312 such that the retaining structures 506 engage with the bottom side 302b. In this manner, the pucks 122 may be "snapped" into the conductive openings 312.

The pucks 122 may be installed manually and/or in an automated fashion. The 122 pucks may be installed from the top side 302a or from the bottom side 302b. When installed from the bottom side 302b, the sensor cable 112 and the grooves 322 may be disposed on the bottom side 302b. In this arrangement, the pucks 122 may be installed into the conductive openings 312 before the sensor cable support device 110 is connected to the PCB 118. When the pucks 122 are installed from the top side 302a, the sensor cable 112 may be connected to the sensor cable support device 110 before or after the sensor cable support device 102 has been connected to the PCB 118.

In some examples, top sides of the pucks 122 may include a substantially planar area (e.g., greater than 1 mm^2). This topside area may be suitable sized and suitably flat to allow a suction head of a robotic placement device (e.g., a pick and place device) to grasp the pucks 122 and place the pucks into the conductive openings 312 and thereby physically support and electrically couple the sensor cable 112 to the electrical traces 306.

Figure 7:
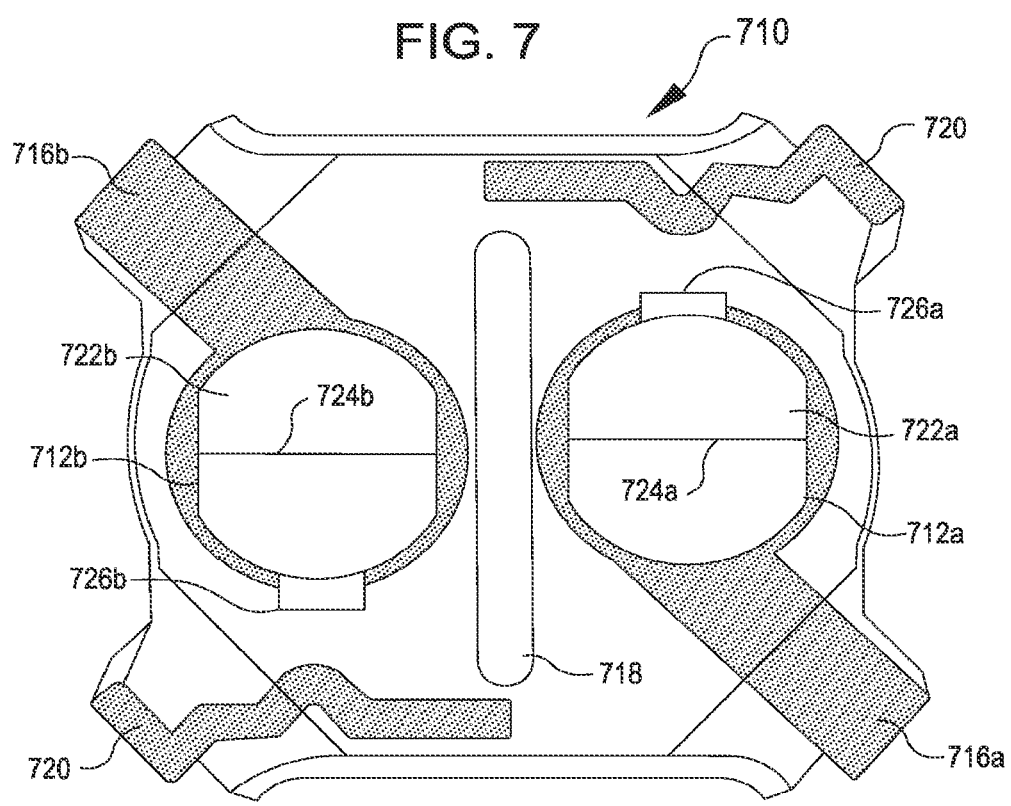
FIG. 7 illustrates a top view of a sensor cable support device, according to at least one example.

FIG. 7 illustrates a top view of a sensor cable support device 710, according to at least one example. The sensor cable support device 710 includes a pair of conductive openings 712a, 712b. Within the conductive openings 712a, 712b are a pair of pucks 722a, 722b. In the example illustrated by FIG. 7, the pucks 722 have been installed from the bottom side of the sensor cable support device 710. Thus, slits 724a, 724b are visible in the view presented in FIG. 7. The sensor cable support device 710 also includes alignment grooves 726a, 726b. The alignment grooves 726 may be used to align the pucks 722 during installation into the conductive openings 712. In some examples, the alignment grooves 726 help retain the pucks 722 after installation. The sensor cable support device 710 also includes electrical traces 716a, 716b, which are respectively connected to the conductive openings 712a, 712b. The sensor cable support device 710 also includes an electrical guard structure 718 disposed between the conductive openings 712 and guard traces 720a, 720b. In some examples, the electrical guard structure 718 may be a recessed channel and/or may be a through hole. In any event the electrical guard structure 718 may function to minimize leakage between the conductive conductive openings 712. The guard traces 720a, 720b may perform a similar function as the electrical guard structure 718.

Figure 8:
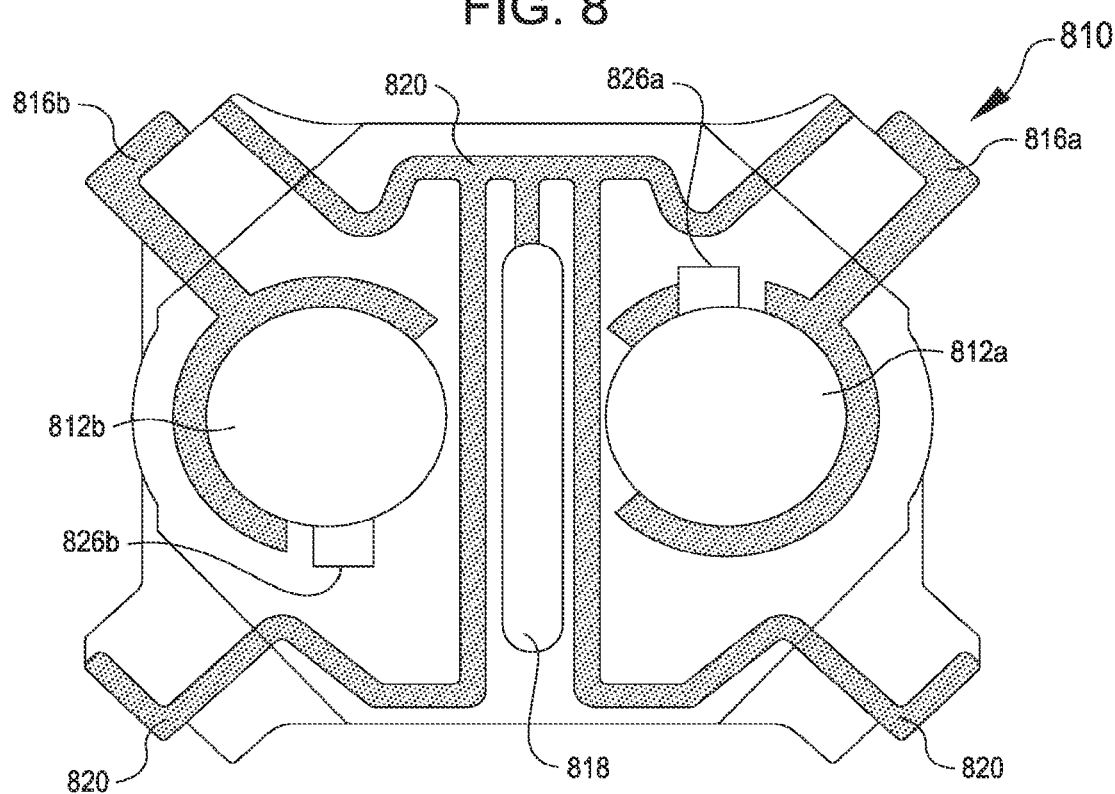
FIG. 8 illustrates a top view of a sensor cable support device, according to at least one example.
Figure 9:
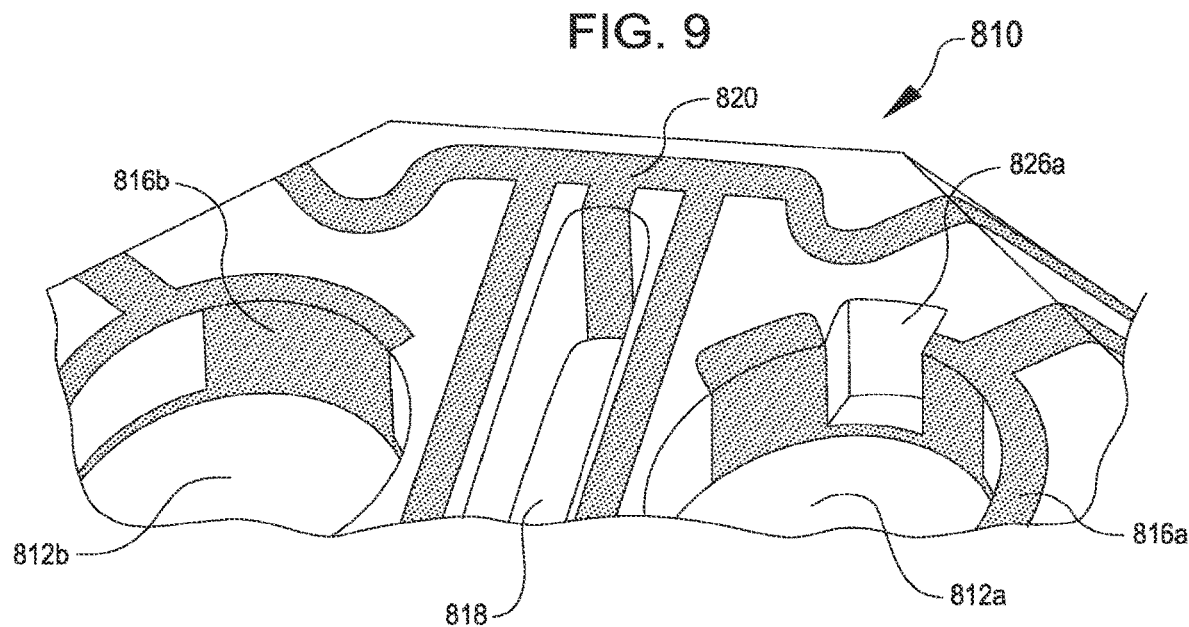
FIG. 9 illustrates a top, perspective view of the sensor cable support device of FIG. 8, according to at least one example.

FIGS. 8 and 9 respectively illustrate a top view and a top, perspective view of a sensor cable support device 810, according various examples. The sensor cable support device 810 includes a pair of conductive openings 812a, 812b. The conductive openings 812, which include a portion thereof coated in conductive material, are electrically coupled to electrical traces 816a, 816b. As illustrated, in some examples, only a portion of the conductive openings 812 includes conductive material. The sensor cable support device 810 also includes alignment grooves 826a, 826b. The alignment grooves 826 may be used to align pucks during installation into the conductive openings 812. In some examples, the alignment grooves 826 help retain the pucks after installation. The sensor cable support device 810 also includes an electrical guard structure 818 and a guard trace 820. In this example, the guard trace 820 may include a more intricate pattern that includes at least two individual traces that extend between the conductive openings 812. The guard trace 820 also extends into the electrical guard structure 818 and down all four legs of the sensor cable support device 810 and/or down two legs.

Figure 10:
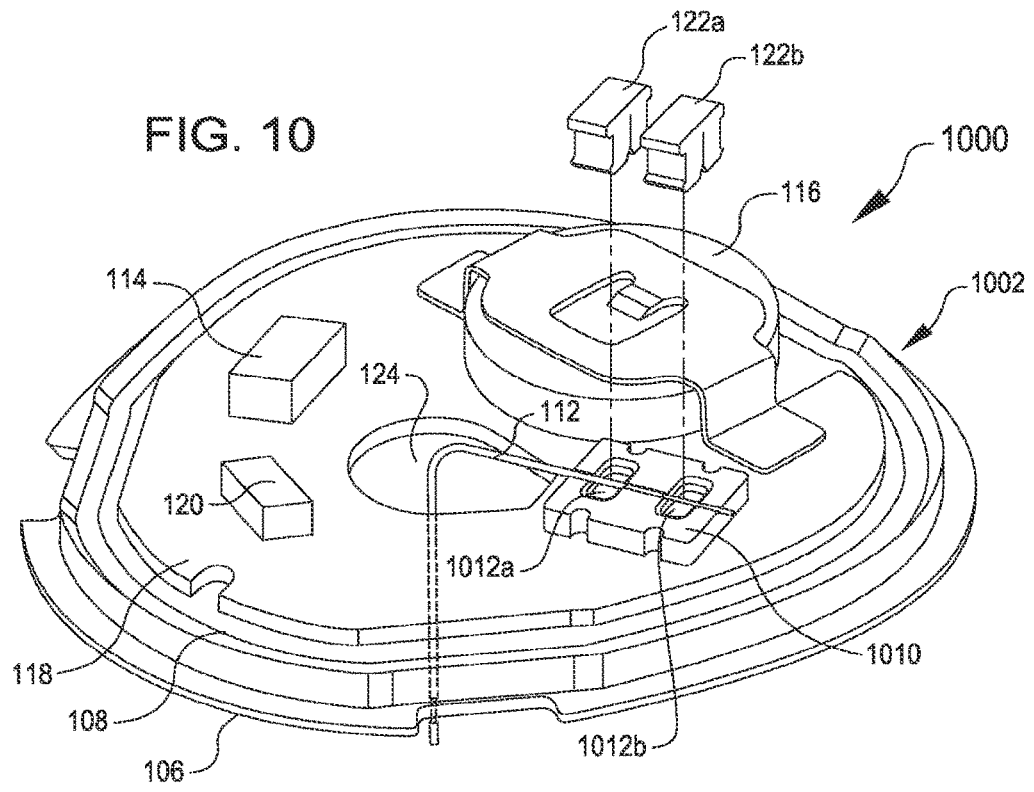
FIG. 10 illustrates a partially exploded view of a monitoring device including an integrated sensor cable support device, according to at least one example.

FIG. 10 illustrates a partially exploded view of a monitoring device 1000 including an integrated sensor cable support device 1010, which is part of biosensor 1002, according to at least one example. The monitoring device 1000 is an example of the monitoring device 100 described herein. Thus, the monitoring device 1000 includes bottom enclosure 106, the moisture barrier 108, the PCB 118, the antenna 120, the sensing circuitry 114, and the power source 116. The sensor cable support device of the monitoring device 1000 has been integrated into the PCB 118. In particular, the sensor cable support device 1010 has been printed in the same manner (e.g., using the same manufacturing techniques) as the PCB 118. Thus, the integrated sensor cable support device 1010 is integrated in the sense that it is integrated into the PCB 118.

The integrated sensor cable support device 1010 includes a pair of conductive openings 1012a, 1012b sized and configured to receive the pucks 122a, 122b. In some examples, the pair of conductive openings 1012a, 1012b may not extend through the PCB 118. In other words, because the integrated sensor cable support device 1010 is effectively mounted directly to the PCB 118, the conductive openings 1012 may be cavities into which the pucks 122 may be installed. Like in other examples described herein, the pucks 122 may function to electrically and mechanically connect the sensor cable 112 to the sensor cable support device 1010.

In the following, further examples are described to facilitate the understanding of the present disclosure.

Example 1

In this example, there is provided a device, including:

a rigid body having a pair of openings, each opening sized and configured to receive a conductive puck, the rigid body configured to support a proximal end of the sensor cable and electrically couple the sensor cable with sensing circuitry of a monitoring device;

a set of rigid legs connected to the rigid body and extending away from a bottom side of the rigid body;

a first electrical trace electrically coupling a first opening of the pair of openings and a distal end of a first leg of the set of legs; and a second electrical trace electrically coupling a second opening of the pair of openings and a distal end of a second leg of the set of legs.

Example 2

In this example, there is provided a device of any of the preceding or subsequent examples, wherein a groove is formed on the bottom side of the rigid body or on a top side of the rigid body that is opposite the bottom side, the groove sized and configured to accommodate the sensor cable.

Example 3

In this example, there is provided a device of any of the preceding or subsequent examples, wherein the groove defines:

a first region disposed adjacent to the first opening, the first region having a first cross-sectional area and sized to accommodate a first portion of the sensor cable including a first wire; and a second region disposed adjacent to the second opening, the second region having a second cross-sectional area and sized to accommodate a second portion of the sensor cable including a second wire, the first cross-sectional area different from the second cross-sectional area.

Example 4

In this example, there is provided a device of any of the preceding or subsequent examples, further including an electrical guard structure disposed between the pair of openings.

Example 5

In this example, there is provided a device of any of the preceding or subsequent examples, wherein the electrical guard structure comprises a third electrical trace that extends to a distal end of a third leg of the set of legs.

Example 6

In this example, there is provided a device of any of the preceding or subsequent examples, wherein the electrical guard structure comprises a guard opening formed in the rigid body and extending through the rigid body.

Example 7

In this example, there is provided a device of any of the preceding or subsequent examples, wherein the set of rigid legs is integral to the rigid body.

Example 8

In this example, there is provided a device of any of the preceding or subsequent examples, wherein the pair of openings extend through the rigid body.

Example 9

In this example, there is provided a device of any of the preceding or subsequent examples, wherein the rigid body includes conductive plating within the pair of openings.

Example 10

In this example, there is provided a device of any of the preceding or subsequent examples, wherein the first opening is electrically isolated from the second opening.

Example 11

In this example, there is provided a device of any of the preceding or subsequent examples, wherein:

the rigid body and the set of legs have characteristics of having been formed from a first material using an injection molding technique; and the first and second electrical traces have characteristics of having been formed using a laser direct structuring technique, the first and second electrical traces including a second material.

Example 12

In this example, there is provided a device, including:

a printed circuit board disposed in a housing having an exterior surface for positioning the wearable monitoring device on skin of a person;

sensing circuitry including one or more electronic components connected to the printed circuit board; and a sensor holder system, including:

a body having a set of legs that extends from one side of the body, the sensor holder system physically coupled to the printed circuit board via the set of legs, the body having a pair of conductive openings formed therein, the pair of conductive openings being electrically coupled to the printed circuit board;

a sensor cable electrically coupled to the sensing circuitry and including a first portion in electrical contact with a first conductive opening of the pair of conductive openings to form a first electrical connection and a second portion in electrical contact with a second conductive opening of the pair of conductive openings to form a second electrical connection; and a pair of pucks installed in the pair of conductive openings such that a first puck of the pair of pucks mechanically retains the first portion in electrical contact with the first conductive opening and a second puck of the pair of pucks mechanically retains the second portion in electrical contact with the second opening.

Example 13

In this example, there is provided a device of any of the preceding or subsequent examples, wherein the pair of pucks is formed from a conductive material.

Example 14

In this example, there is provided a device of any of the preceding or subsequent examples, wherein the pair of pucks, when installed in the pair of conductive openings, contribute to the first electrical connection and the second electrical connection.

Example 15

In this example, there is provided a device of any of the preceding or subsequent examples, wherein each puck of the pair of pucks defines a slit; the first portion of the sensor cable is held within a first slit of the first puck when the first puck is installed in the first conductive opening; and the second portion of the sensor cable is held within a second slit of the second puck when the second puck is installed in the second conductive opening.

Example 16

In this example, there is provided a device of any of the preceding or subsequent examples, wherein the sensor cable includes a distal end that extends to a position beyond the exterior surface of the housing.

Example 17

In this example, there is provided a device of any of the preceding or subsequent examples, wherein the first portion of the sensor cables extends across the first conductive opening and is in physical contact with the first conductive opening at two or more locations.

Example 18

In this example, there is provided a device of any of the preceding or subsequent examples, wherein the sensor cable includes a first electrode corresponding to the first portion and a second electrode corresponding to the second portion.

Example 19

In this example, there is provided a device of any of the preceding or subsequent examples, wherein the sensor holder system further includes an electrical guard structure disposed between the pair of openings, the electrical guard structure including at least one of an electrical trace or an opening formed in the body.

Example 20

In this example, there is provided a device of any of the preceding or subsequent examples, wherein the pair of conductive openings is electrically coupled to the printed circuit board via a pair of electrical traces extending between distal ends of a pair of legs of the set of legs and the pair of conductive openings.

Example 21

In this example, there is provided a device of any of the preceding or subsequent examples, wherein the sensing circuitry is configured to sense biological information about the person via a pair of electrodes of the sensor cable that is inserted into the person's skin.

Example 22

In this example, there is provided a device of any of the preceding or subsequent examples, wherein the housing includes a top enclosure and a bottom enclosure, the exterior surface defined on the bottom enclosure.

Example 23

In this example, there is provided a device of any of the preceding or subsequent examples, wherein the top enclosure physically contacts outward-facing sides of the pair of pucks and the bottom enclosure physically contacts a bottom side of the circuit board.

Example 24

In this example, there is provided a system, including:

a sensor cable including a first portion insertable into skin of a person, the first portion including means for generating glucose information; and a sensor holder system, including:

alignment means for physically aligning a second portion of the sensor cable;

retaining means for physically retaining the second portion of the sensor cable;

support means for physically supporting the alignment means and the retaining means; and coupling means for electrically coupling the second portion of the sensor cable to circuitry disposed on a printed circuit board for determining an analyte level for the person (e.g., glucose or other analyte).

Example 25

In this example, there is provided a system of any of the preceding or subsequent examples, wherein the alignment means defines at least one of a groove or a set of opposing tabs.

Example 26

In this example, there is provided a system of any of the preceding or subsequent examples, wherein the retaining means includes a pair of conductive pucks configured to physically couple with the support means.

Example 27

In this example, there is provided a system of any of the preceding or subsequent examples, wherein the support means includes a rigid body connected to a set of rigid legs extending between the rigid body and the printed circuit board.

Example 28

In this example, there is provided a system of any of the preceding or subsequent examples, wherein the coupling means includes one or more electrical traces disposed on the support means.

Example 29

In this example, there is provided a system of any of the preceding or subsequent examples, wherein the means for generating the glucose information includes one or more electrodes configured to generate electrical signals corresponding to an amount of glucose present within interstitial fluid beneath the skin of the person.

Example 30

In this example, there is provided a system, including:
a sensor cable support device, including:
a body having a pair of conductive openings;
a set of legs extending away from a bottom side of the body; and
a pair of electrical traces extending between the pair of conductive openings and distal ends of a pair of legs of the set of legs;
a sensor cable including:
a first portion in electrical contact with a first conductive opening of the pair of conductive openings to form a first electrical connection; and
a second portion in electrical contact with a second conductive opening of the pair of conductive openings to form a second electrical connection; and
a pair of pucks installed in the pair of openings such that a first puck of the pair of pucks mechanically retains the first portion in electrical contact with the first conductive opening and a second puck of the pair of pucks mechanically retains the second portion in electrical contact with the second opening.

Example 31

In this example, there is provided a system of any of the preceding or subsequent examples, wherein the set of legs is adapted for attachment to a printed circuit board.

Example 32

In this example, there is provided a system of any of the preceding or subsequent examples, wherein the first portion of the sensor cable is defined by a first cross-sectional area and the second portion of the sensor cable is defined by a second cross-sectional area that is larger than the first cross-sectional area.

Example 33

In this example, there is provided a system of any of the preceding or subsequent examples, wherein a pair of grooves is formed in a top side of the body, a first groove of the pair of grooves sized and configured to receive the first portion of the sensor cable, and the second groove of the pair of grooves sized and configured to receive the second portion of the sensor cable.

Example 34

In this example, there is provided a system of any of the preceding or subsequent examples, wherein the sensor holder device is integrated into a printed circuit board such that the sensor holder device and the printed circuit board are formed using printed circuit board manufacturing technique The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Use herein of the word "or" is intended to cover inclusive and exclusive OR conditions. In other words, A or B Or C includes any or all of the following alternative combinations as appropriate for a particular usage: A alone; B alone; C alone; A and B only; A and C only; B and C only; and all three of A and B and C.

What is claimed is:

1. A support device for supporting a sensor cable, the support device, comprising:
   a rigid body defining a pair of openings, each opening sized and configured to receive a conductive puck, the rigid body configured to support a proximal end of the sensor cable and electrically connect the sensor cable with sensing circuitry of a monitoring device;
   a set of rigid legs connected to the rigid body and extending away from bottom side of the rigid body;
   a first electrical trace electrically connecting a first opening of the pair of openings and a distal end of a first leg of the set of rigid legs; and
   a second electrical trace electrically connecting a second opening of the pair of openings and a distal end of a second leg of the set of rigid legs.

2. The support device of claim 1, wherein the set of rigid legs is integral to the rigid body.

3. The support device of claim 1, wherein the pair of openings extend through the rigid body.

4. The support device of claim 1, wherein the rigid body comprises conductive plating within the pair of openings.

5. The support device of claim 1, wherein the first opening is electrically isolated from the second opening.

6. The support device of claim 1, wherein:
   the rigid body and the set of rigid legs have characteristics of having been formed from a first material using an injection molding technique; and
   the first and second electrical traces have characteristics of having been formed using a laser direct structuring technique, the first and second electrical traces comprising a second material.

7. The support device of claim 1, wherein the rigid body is further configured to position distal end of the sensor cable that is insertable into a person's skin.

8. The support device of claim 1, wherein a groove is formed on the bottom side of the rigid body or on a top side of the rigid body that is opposite the bottom side, the groove sized and configured to accommodate the sensor cable.

9. The support device of claim 8, wherein the groove defines:
   a first region disposed adjacent to the first opening, the first region having a first cross-sectional area and sized to accommodate a first portion of the sensor cable including a first wire; and
   a second region disposed adjacent to the second opening, the second region having a second cross-sectional area and sized to accommodate a second portion of the sensor cable including a second wire, the first cross-sectional area different from the second cross-sectional area.

10. The support device of claim 1, further comprising an electrical guard structure disposed between the pair of openings.

11. The support device of claim 10, wherein the electrical guard structure comprises a third electrical trace that extends to a distal end of a third leg of the set of rigid legs.

12. The support device of claim 10, wherein the electrical guard structure comprises a guard opening formed in the rigid body and extending through the rigid body.

* * * * *